United States Patent
Palermo

(10) Patent No.: US 9,499,778 B2
(45) Date of Patent: Nov. 22, 2016

(54) AUTOMATED INTRACYTOPLASMIC SPERM INJECTION ASSISTED FERTILIZATION SYSTEM

(71) Applicant: Cornell University, Ithaca, NY (US)

(72) Inventor: Gianpiero D. Palermo, New York, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 233 days.

(21) Appl. No.: 14/514,474

(22) Filed: Oct. 15, 2014

(65) Prior Publication Data

US 2015/0031012 A1    Jan. 29, 2015

Related U.S. Application Data

(63) Continuation of application No. PCT/US2013/036801, filed on Apr. 16, 2013.

(60) Provisional application No. 61/624,490, filed on Apr. 16, 2012.

(51) Int. Cl.
| | |
|---|---|
| A61B 17/425 | (2006.01) |
| C12M 3/00 | (2006.01) |
| C12M 3/06 | (2006.01) |
| A61D 19/02 | (2006.01) |

(52) U.S. Cl.
CPC ............ *C12M 21/06* (2013.01); *A61B 17/425* (2013.01); *C12M 23/16* (2013.01); *C12M 23/42* (2013.01); *A61D 19/02* (2013.01)

(58) Field of Classification Search
CPC .............. C12M 21/06; A61B 17/425–17/435; A61D 19/00–19/04
See application file for complete search history.

(56) References Cited

U.S. PATENT DOCUMENTS

| | | | |
|---|---|---|---|
| 6,695,765 B1 | 2/2004 | Beebe et al. | |
| 7,390,648 B1 * | 6/2008 | Palacios-Boyce | C12M 21/06 422/64 |
| 2006/0270021 A1 * | 11/2006 | Takayama et al. | B01L 3/50273 435/283.1 |
| 2010/0234674 A1 | 9/2010 | Wheeler et al. | |
| 2011/0250690 A1 * | 10/2011 | Craig | A01N 1/02 435/404 |

FOREIGN PATENT DOCUMENTS

| | | |
|---|---|---|
| WO | 03/014291 A1 | 2/2003 |
| WO | 2011/16340 A1 | 12/2011 |
| WO | 2012/037642 A1 | 3/2012 |

OTHER PUBLICATIONS

European Supplementary Search Report for EP Application No. 13778930 mailed Oct. 7, 2015 (7 pages).
Beebe et al., "Microfluidic Technology for Assisted Reproduction," Theriogenology, 2002, 57:125-135.
Lopez-Garcia et al., "Sperm Motion in a Microfluidic Fertilization Device," Biomed Microdevices, 2008, 10:709-718.
Meseguer et al., "Full in vitro Fertilization Laboratory Mechanization:Toward Robotic Assisted Reproduction?," Conceptions, 2012, 97(6):1277-1286.
European Office Action for EP Application No. 13778930 mailed Jun. 15, 2016 (4 pages).
PCT International Search Report for PCT Application No. PCT/US2013/036801 mailed Jul. 23, 2013 (3 pages).
PCT Written Opinion of the International Search Authority for PCT/US2013/036801 mailed Jul. 23, 2013 (5 pages).

\* cited by examiner

*Primary Examiner* — Catherine B Kuhlman
(74) *Attorney, Agent, or Firm* — Sutherland Asbill & Brennan LLP

(57) ABSTRACT

An integrated automated system comprising a microfluidic cassette, and methods of use thereof, for intracytoplasmic sperm injection assisted fertilization. The microfluidic cassette and the integrated automated system provides a complete set-up of human gametes for assisted in vitro fertilization, including proper cell stage recognition, gamete propulsion via microfluidic currents, microinjection of a spermatozoon into an oocyte, and subsequent embryo culture and monitoring, thus allowing widespread distribution of in vitro insemination by favoring affordability.

20 Claims, 14 Drawing Sheets

AUTOMATED INTRACYTOPLASMIC SPERM INJECTION ASSISTED FERTILIZATION SYSTEM

CROSS-REFERENCE TO RELATED APPLICATIONS

This application is a continuation of PCT Application No. PCT/US2013/036801 filed Apr. 16, 2013 which claims priority to U.S. Provisional Application Ser. No. 61/624,490 filed Apr. 16, 2012, the entire contents of which are incorporated by reference herewith.

FIELD OF THE INVENTION

The invention relates to a device and system using a microfluidic platform for assisted reproduction. More specifically, the invention relates to an integrated automated fertilization system comprising a microfluidic device cassette, and methods of use thereof, for in vitro oocyte cumulus removal, oocyte maturation, sperm selection and intracytoplasmic injection, and in vitro fertilization and embryo culture and development.

BACKGROUND OF THE INVENTION

In the 1970s the introduction of in vitro procedures allowed creation of the human embryo outside the body aimed at treating couples with tubal factor infertility. The early successes achieved with assisted reproductive technologies (ART), although modest, motivated the ambition to improve efficiency on one hand and to extend treatment to other infertility indications. It was this intense effort to address fertilization failure plaguing early assisted fertilization cycles that brought to the development of intracytoplasmic sperm injection (ICSI) in 1992. This in vitro procedure has allowed clinicians to pinpoint the initial steps involved in the interaction of the parental gametes.

The reliability of sperm injection practices in term of high and consistent fertilization rates has allowed the generous application worldwide of this gamete insemination method. ICSI is now carried out in at least 53 countries and has currently generated about 2 million babies. This popular utilization unfortunately has not been accompanied by an increased affordability nor by an improved access through health insurances. Moreover, the inconsistency of the outcome for the reported data from different countries would call for an improved standardization with enhanced quality control. However, ICSI although it was developed as a treatment for male infertility, it has become the preferred method of insemination being performed in large centers at a rate of over 70%. Therefore, the development of an automated system is desirable that perform ICSI would become the sole in vitro insemination method.

Cho et al have described a gravity-driven pumping system to sort sperm samples (Cho et al. 2003, Passively driven integrated microfluidic system for separation of motile sperm, Anal Chem. 75(7):1671-1675). The device, termed a microscale integrated sperm sorter (MISS), contains inlet/outlet ports, fluid reservoirs, gravity-driven power sources, and converging microchannels with laminar flow, all integrated components working together to facilitate sperm sorting. This device was designed so a converging stream of semen and media would flow in parallel, in a laminar fashion within a microchannel. The two parallel streams only mix by diffusion at the interface between streams, but motile sperm are able to swim across the contacting streamline and into the media for collection. Nonmotile sperm, cellular debris, and seminal plasma do not cross this barrier and are shuttled into a waste reservoir.

Suh et al have described initial efforts to create some microfluidic components, namely for sperm selection, oocyte handling, microinsemination (but not ICSI), and embryo manipulation and culture, as well as the need for and benefits of integrated systems (Suh et al. 2003, Rethinking gamete/embryo isolation and culture with microfluidics, Hum Reprod Update. 9(5):451-61; Suh et al. 2005, Microfluidic Applications for Andrology, J Androl. 26(6):664-70).

Smith et al have provided a review in 2011 that discusses sperm selection and speculates on microinsemination of mouse oocytes and embryo culture (Smith et al. 2011, Microfluidics for gametes, embryos, and embryonic stem cells, Semin Reprod Med. 29(1):5-14). Smith is cofounder of the medical device company, Incept BioSystems™, which is using its "System for Microfluidic Assisted Reproductive Technology (SMART)" to create microfluidic IVF systems. Its first product is a device for embryo culture.

Unisense FertiliTech A/S markets an automated embryo incubator that incorporates a fully stable incubation environment with integrated respiration and time-lapse image acquisition; the latter allows embryo assessment (Raty et al. 2004, Lab on a Chip, 4:186-190).

Lu et al have described a disposable chip placed on a microscope where sperm and oocytes are placed into 2 separate chambers; a spermatozoon is selected and robotized ICSI performed on all oocytes executed by a human operator (Lu et al. 2011, Robotic ICSI, IEEE Trans Biomed Eng, 58:2102-2108). Adamo and Jensen also demonstrated proof of concept for microinjection of a fluorescent dye into a single cell (Adamo and Jensen 2008, Lab on a Chip, 8:1258-1261).

The devices described in the prior art perform different aspects of in vitro insemination ranging from sperm and oocyte preparation to actual insemination followed by embryo culture. Although the aforementioned prior art describes efforts to generate components of a complete, automated system, no such system has been created.

SUMMARY OF THE INVENTION

The invention provides an integrated automated system for performing assisted fertilization using ICSI starting from oocyte cumulus removal, sperm selection and immobilization, ICSI injection, and embryo culture and selection. This automated system provides widespread distribution of in vitro insemination by favoring affordability.

In certain embodiments, the invention provides a disposable enclosed microfluidics cassette device for intracytoplasmic sperm injection assisted fertilization comprising: a) an oocyte reservoir comprising an oocyte chamber, an inlet and an outlet; b) an oocyte cumulus removal channel in selective fluid communication with the oocyte reservoir outlet; c) an oocyte immobilizing station in selective fluid communication with the oocyte cumulus removal channel; d) a spermatozoa reservoir comprising a spermatozoa chamber, an inlet and outlet; e) a motile spermatozoa isolating channel in selective fluid communication with the spermatozoa reservoir outlet; f) a motile spermatozoa immobilization station in selective fluid communication with the motile spermatozoa isolating channel and in selective fluid communication with the oocyte immobilization station; and g) an embryo culturing chamber in selective fluid communication with the oocyte immobilization station.

In certain embodiments, a downstream portion of the oocyte cumulus removal channel of the enclosed microfluidics cassette device can have a narrower width than the oocyte chamber allowing individual progression of oocyte. In certain embodiments, a portion of the oocyte cumulus removal channel has a width of about 200 μm. In other embodiments, the oocyte cumulus removal channel has one or more 90° turns allowing rotation of an oocyte to remove cumulus cells. In certain embodiments, the oocyte cumulus removal channel of the enclosed microfluidic cassette device has a valved cumulus waste outlet in selective fluid communication therewith.

In certain embodiments, the motile spermatozoa isolating channel in the enclosed microfluidic cassette device of the invention has a non-motile spermatozoa outlet or holding chamber in selective fluid communication therewith. In other embodiments, the motile spermatozoa immobilization station comprises an intracytoplasmic sperm injection system.

In other embodiments, the enclosed microfluidic cassette device also comprises a plurality of upstream oocyte reservoirs in downstream selective fluid communication with a plurality of oocyte cumulus removal channels, which in turn are in downstream selective fluid communication with the oocyte immobilization station. In certain embodiments, the enclosed microfluidic cassette device further comprises a plurality of downstream embryo culturing chambers in selective fluid communication with the oocyte immobilization station.

In certain embodiments, the selective fluid communication in each component of the enclosed microfluidic cassette device can be controlled by one or more piezoelectric gates comprising nanoelectrode modules. In certain embodiments, one or more observation stations for monitoring and evaluating oocytes, sperm, and embryos are encompassed in each channel, reservoir, chamber, inlet, outlet, station or component in the enclosed microfluidic cassette device.

The invention further provides a system for automated intracytoplasmic sperm injection (ICSI) assisted fertilization comprising the enclosed microfluidic cassette device of the invention and a machine for functionally engaging the microfluidics cassette device comprising a central processing unit (CPU) and software for automated monitoring and control of the ICSI process, including the selective communication between connected channels, chambers, reservoirs, inlets, outlets, for progression of microfluidics, oocytes, oocyte cumulus removal, oocyte selection and immobilization, motile spermatozoa isolation, motile spermatozoa immobilization, intracytoplasmic sperm injection, and embryo culturing.

In certain embodiments, the machine of the inventive automated system for intracytoplasmic sperm injection assisted fertilization further comprises a plurality of digital video cameras and associated remote video monitors connected to the CPU. In certain embodiments, the CPU and related software automatically controls the temperature and internal pressure of the device and the addition of cellular media, such as via the oocyte reservoir inlet, the spermatozoa reservoir inlet, or the embryo development chamber.

In some embodiments, the machine of the inventive automated system for intracytoplasmic sperm injection assisted fertilization controls the oocyte immobilizing station by creating negative pressure through a microchannel in the oocyte immobilizing station. In some embodiments, the machine of the inventive automated system for intracytoplasmic sperm injection assisted fertilization controls the intracytoplasmic sperm injection by applying an electric field from a pizeo-pipette to penetrate the oocyte and then applying microfluidic pressure inside the pizeo-pipette to position the spermatozoa into the oocyte.

The invention also provides a method for automated intracytoplasmic sperm injection assisted fertilization comprising: combining a spermatozoa and an oocyte in a continuous path microfluidics cassette device engaged with the machine for its operation within the disclosed system.

DETAILED DESCRIPTION OF THE INVENTION

Figure 1:
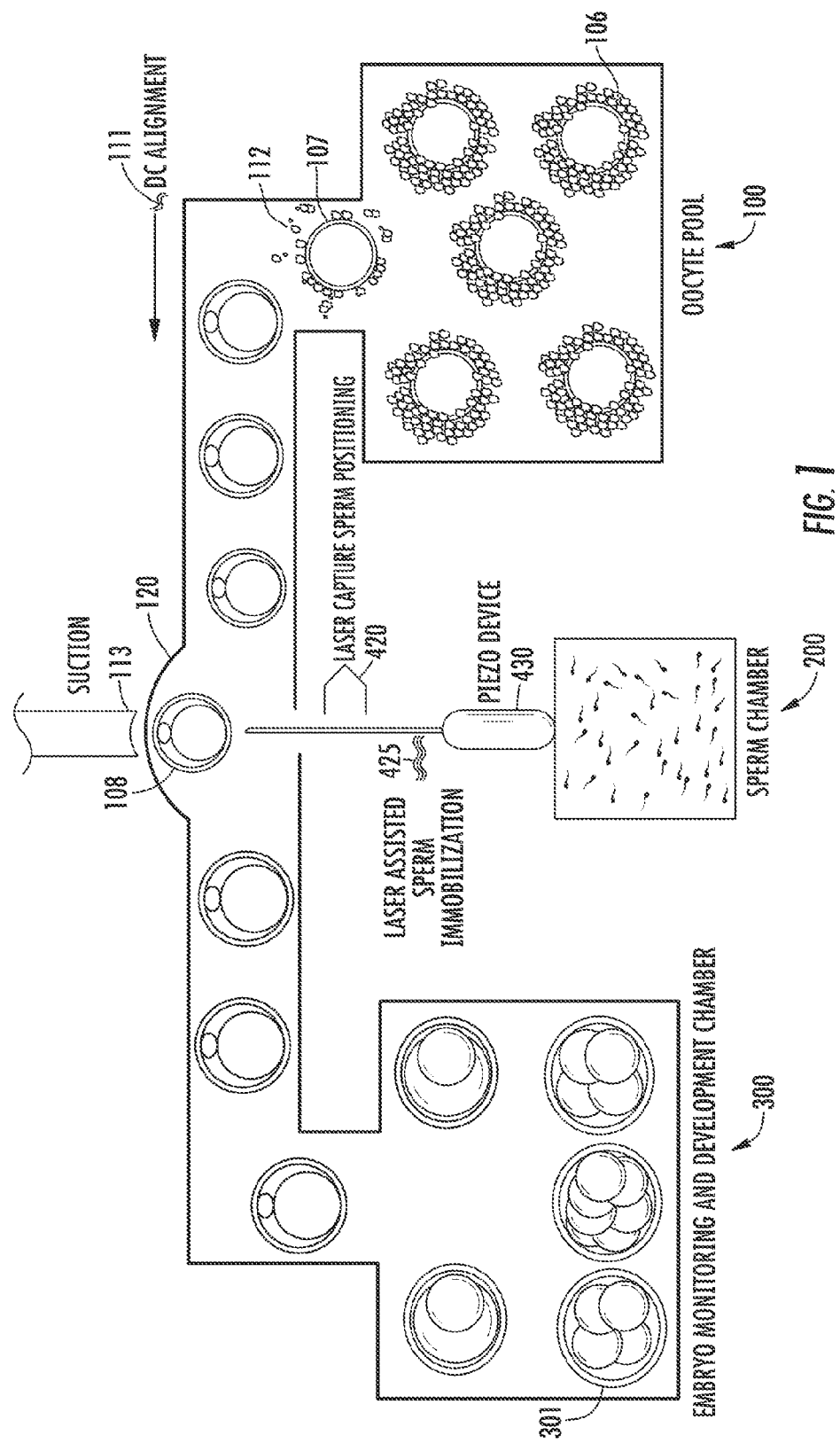
FIG. 1 shows a schematic of an embodiment of the invention in top view, comprising sperm and oocyte chambers, a piezo device, a region in which the cumulus-oocyte complex is decoronized and cumulus cells are removed; a region in which the oocyte is demobilized (a configuration of vacuum channel for said demobilization) and the sperm injected, and an embryo monitoring and development chamber. Further depicted are a pipette for injecting the sperm; a laser sperm immobilization device; and a laser sperm capture and positioning device.
Figure 2:
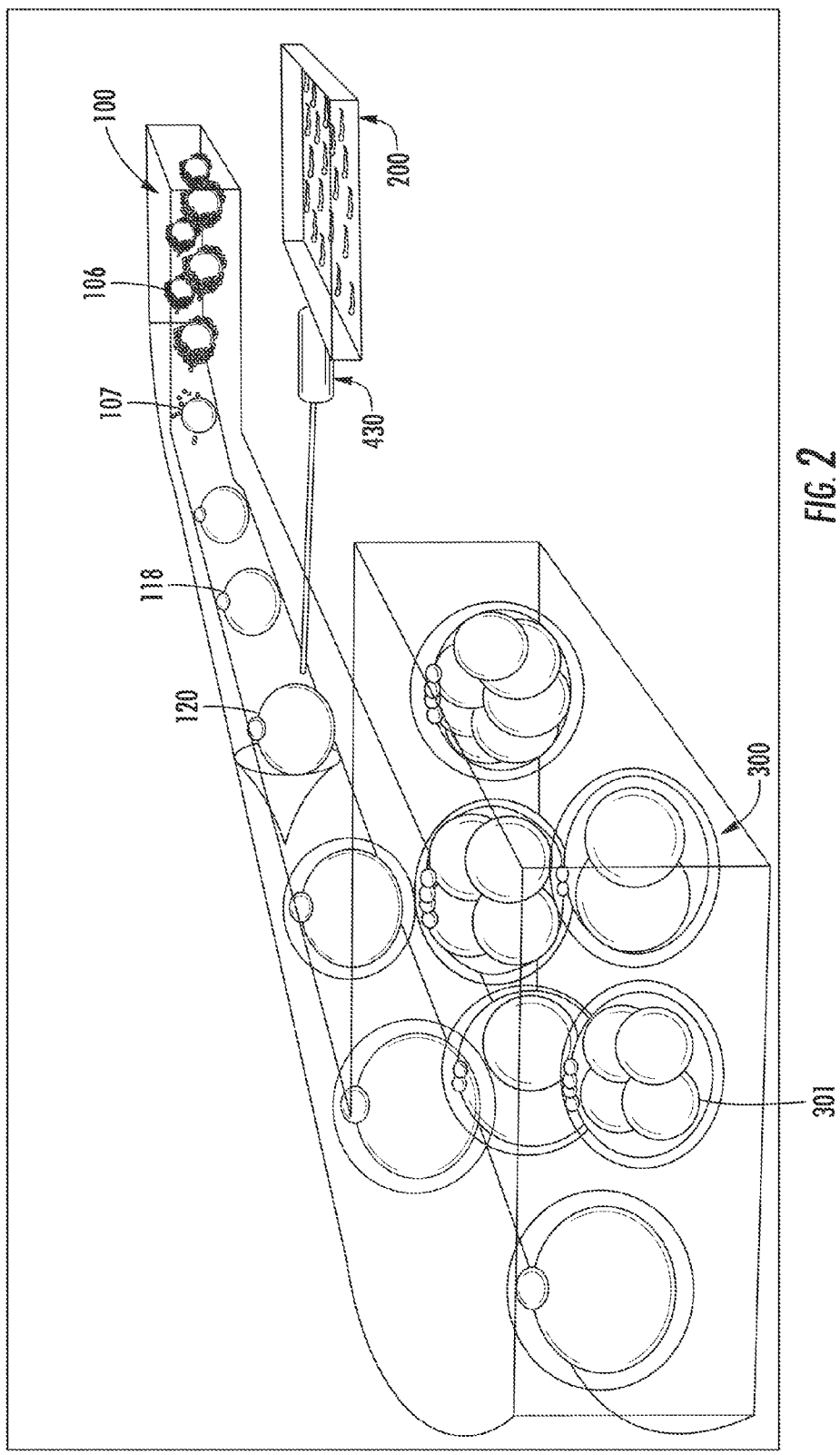
FIG. 2 shows the system of FIG. 1 in orthogonal view.

In the following description, reference is made to the accompanying drawings that form a part hereof, and in which is shown by way of illustration specific embodiments which may be practiced. These embodiments are described in detail to enable those skilled in the art to practice the invention, and it is to be understood that other embodiments may be utilized and that logical changes may be made without departing from the scope of the present invention. The following description of example embodiments is, therefore, not to be taken in a limited sense, and the scope of the present invention is defined by the appended claims.

The Abstract is provided to comply with 37 C.F.R. §1.72(b) to allow the reader to quickly ascertain the nature and gist of the technical disclosure. The Abstract is submitted with the understanding that it will not be used to interpret or limit the scope or meaning of the claims.

The invention provides a microfluidic ICSI automated system which provides a complete assisted fertilization set-up starting from sperm preparation all the way to embryo culture. This automated system provides for widespread distribution of in vitro insemination by favoring affordability. Certain embodiments of the invention include, but are not limited to, features of a COC-MII oocyte wash chamber to facilitate decoronization and removal of cumulus cells; laser-assisted gamete immobilization and alignment in conjunction with an automated injection system, and an electric current-facilitated cellular alignment.

In certain embodiments, the invention provides an enclosed microfluidics cassette device for intracytoplasmic sperm injection assisted fertilization comprising: a) an oocyte reservoir comprising an oocyte chamber, an inlet and an outlet; b) an oocyte cumulus removal channel in selective fluid communication with the oocyte reservoir outlet; c) an oocyte immobilizing station in selective fluid communication with the oocyte cumulus removal channel; d) a spermatozoa reservoir comprising a spermatozoa chamber, an inlet and outlet; e) a motile spermatozoa isolating channel in selective fluid communication with the spermatozoa reservoir outlet; f) a motile spermatozoa immobilization station in selective fluid communication with the motile spermatozoa isolating channel and in selective fluid communication with the oocyte immobilization station; and g) an embryo culturing chamber in selective fluid communication with the oocyte immobilization station.

To facilitate an understanding of the present invention, a number of terms and phrases are defined below. As used herein, "a" or "an" means one or more than one depending upon the context in which it used.

As used herein, microfluidics addresses the behavior, specific control, and manipulation of microliter and nanoliter volumes of fluid. Microfluidic systems are designed for a unidirectional flow of oocytes, embryos, sperm, medium, and medium components at various discrete strategies of the ICSI process. Exemplary, non-limited examples of microfluidic devices and the materials and techniques used for construction of components of the microfluidic devices are described, e.g., Smith et al., 2011, Microfluidic for Gametes, Embryos, and Embryonic Stem Cells, Semin Reprod Med 29(1):5-14; and US 2013/0034906 to Smith et al., each of which is herein incorporated by reference in its entirety.

As used herein, the term "oocyte" refers to a female gametocyte, female gamete, germ cell involved in reproduction, an immature ovum, or egg cell. Preferred sperm for use in the invention are mammalian, including but not limited to human, livestock (including but not limited to bovine, porcine, and ovine) and companion animal (including but not limited to canine and feline).

As used herein, the term "cumulus cell" refers to a cell in the developing ovarian follicles which is in direct or close proximity to an oocyte. The cumulus cells are granulosa cells surround the oocyte both in the ovarian follicle and after ovulation. As used herein, the term "cumulus-oocyte complex" refers to at least one oocyte and at least one cumulus cell in physical association with each other.

As used herein, the term "oocyte maturation" refers to biochemical events that prepare an oocyte for fertilization. Such processes may include but are not limited to the completion of meiosis II. The term "oocyte nuclear maturation" specifically refers to such completion of meiosis II. The term "oocyte cytoplasmic maturation" specifically refers to cytoplasmic events that occur to instill upon the oocyte a capacity to complete nuclear maturation, insemination, and/or early embryogenesis. Oocyte cytoplasmic maturation events may include but are not limited to accumulation of mRNA, proteins, substrates, and nutrients that are required to achieve the oocyte developmental competence that fosters embryonic developmental competence.

As used herein, the term "sperm" or "spermatozoa" refers to a male reproductive gamete or male gametocyte. A uniflagellar sperm cell that is motile is also referred to as a spermatozoon, whereas a non-motile sperm cell is also referred to as a spermatium. Preferred sperm for use in the invention are mammalian, including but not limited to human, livestock (including but not limited to bovine, porcine, and ovine) and companion animal (including but not limited to canine and feline).

As used herein, the term "embryo" refers to an oocyte fertilized with sperm. An embryo is a multicellular diploid eukaryote in its earliest stage of development, from the time of first cell division until birth or germination. In organisms that reproduce sexually, once a sperm fertilizes an egg cell or oocyte, the result cell is called the zygote, which possesses half the DNA of each of its two parents. The zygote will begin to divide by mitosis to produce a multicellular organism called embryo.

As used herein, the term "cell" refers to any eukaryotic cell, including mammalian cells, avian cells, amphibian cells, plant cells, fish cells, and insect cells, whether located in vitro or in vivo. As used herein, the term "cell culture" refers to any in vitro population of cells. Included within this term are continuous cell lines (e.g., with an immortal phenotype), primary cell cultures, transformed cell lines, finite cell lines (e.g., non-transformed cells), and any other cell population maintained in vitro.

As used herein, the term "in vitro" refers to an artificial environment and to processes or reactions that occur within an artificial environment. In vitro environments can consist of, but are not limited to, test tubes and cell culture. The term "in vivo" refers to the natural environment (e.g., an animal or a cell) and to processes or reaction that occur within a natural environment.

As used herein, the term "medium" or "fluid medium" refers to any fluid within a system. In some embodiments, the medium or fluid medium is compatible with cell culture (e.g., supports cell viability; supports cell growth; supports cell development; does not cause toxicity or lethality to a cell).

As used herein, the term "channel," "microchannel," "chamber," "microchamber," and "reservoir," can be used interchangeably, and refer to a structural microfluidic pathway or container. In some embodiments, a channel may comprise a three-dimensional protrusion into the surface of a material. In some embodiments, a channel is elongated in shape (e.g., rectangular prism). The channel is capable of holding or transmitting fluid containing cells or other biologic components. As used herein, the term "dynamic flow" refers to a state in a fluid system in which fluids experience kinetic motion through the system.

As used herein, the term "selective fluid communication" means that a fluid pathway exists between two referenced structures for the passage of materials (i.e., cells in a fluid media), the passage through which can be selectively opened, narrowed, widened or closed by an operator or an automated algorithm controlled by a CPU and software. Selective fluid communication of a microfluidic channel (or between channels, reservoirs, chambers, stations, etc.) can be achieved through systems known and later developed, including piezoelectric gates, physical clamps, electric fields, and fluidics pressure generation.

As used herein, "enclosed" means a microfluidic system that is sealably contained and continuous, although various sealable inlets and outlets may be disposed along the pathway, and temporary occlusions, such as created by piezoelectric gates, may selectively impede the fluid flow between stages, as described herein.

The invention provides an enclosed microfluidics cassette device for intracytoplasmic sperm injection assisted fertilization comprising one or more oocyte chamber and cumulus removal channels. In certain embodiments, a portion of the oocyte cumulus removal channel of the enclosed microfluidics cassette device has a narrower width than the oocyte chamber allowing individual progression of oocyte. In certain embodiments, the portion of the oocyte cumulus removal channel has a width of about 200 µm. In other embodiments, the oocyte cumulus removal channel has at least one 90° turn allowing rotation of an oocyte to remove cumulus cells. In certain embodiments, the oocyte cumulus removal channel of the enclosed microfluidic cassette device has a waste outlet in selective fluid communication therewith. In certain embodiments, the enclosed microfluidic cassette device also comprises a plurality of oocyte reservoirs in selective fluid communication with a plurality of oocyte cumulus removal channels in selective fluid communication with the oocyte immobilization station. In certain embodiments, the enclosed microfluidic cassette device further comprises a plurality of embryo culturing chambers in selective fluid communication with the oocyte immobilization station.

The invention provides an enclosed microfluidics cassette device for intracytoplasmic sperm injection assisted fertilization comprising a spermatozoa reservoir comprising a spermatozoa chamber, an inlet and outlet; a motile spermatozoa isolating channel in selective fluid communication with the sperm reservoir outlet; and a motile spermatozoa immobilization station in selective fluid communication with the motile spermatozoa isolating channel and in selective fluid communication with the oocyte immobilization station. In certain embodiments, the motile spermatozoa isolating channel in the enclosed microfluidic cassette device of the invention has an immotile (or non-motile) spermatozoa outlet in selective fluid communication therewith. In other embodiments, the motile spermatozoa immobilization station comprises an intracytoplasmic sperm injection system.

The microfluidic device of the invention can be designed as a disposable biologics cassette, and can be constructed of any suitable materials, now known and later developed in the art. In certain embodiments, the microfluidic device of the invention can be fabricated with an inert polymeric organosilicon polymer such as the poly(dimethylsiloxane) (PDMS) in which the compositional layering/spinning techniques can forge cellular tunnels and chambers. Soft photolithographic techniques can be used to print the necessary chambers directly on the chip. The fluid handling materials may be nontoxic, insulating, and permeable to gases. PDMS permits submicron fidelity with molding, cures at low temperatures, and can easily seal itself. Valve systems needed to create chamber separation can be membranes that are manipulated by pneumatic characteristics, with air channels being bored into the PDMS matrix.

In certain embodiments, fluids are supplied to, or removed from, the device by any suitable methods. Fluids may, for example, be supplied or removed by syringes, or microtubing attached to or bonded to the inlet channels, etc. Sperm and oocytes may be supplied to the device through inlet channels or other re-sealable ports openings, for example.

Fluid flow may be established by any suitable method. For example, external micropumps suitable for pumping small quantities of liquids are available. Micropumps may also be provided in the device itself, driven by thermal gradients, magnetic and/or electric fields, applied pressure, etc. All these devices are known to the skilled artisan. Integration of passively-driven pumping systems and microfluidic channels are described by Weigl et al., Proceedings of MicroTAS 2000, Enshede, Netherlands, pp. 299-302 (2000), which is herein incorporated by reference by its entirety.

In other embodiments, fluid flow is established by a gravity flow pump, by capillary action, or by combinations of these methods. A simple gravity flow pump consists of a fluid reservoir either external or internal to the device, which contains fluid at a higher level (with respect to gravity) than the respective device outlet. Such gravity pumps have the deficiency that the hydrostatic head, and hence the flow rate, varies as the height of liquid in the reservoir drops. For many devices, a relatively constant and non-pulsing flow is desired.

A gravity-driven pump as disclosed in published PCT Publication No. WO 03/008102, incorporated herein by reference, may be used. In such devices, a horizontal reservoir is used in which the fluid moves horizontally, being prevented from collapsing vertically in the reservoir by surface tension and capillary forces between the liquid and reservoir walls. Since the height of liquid remains constant, there is no variation in the hydrostatic head.

Flow may also be induced by capillary action. In such a case, fluid in the respective outlet channel or reservoir will exhibit greater capillary forces with respect to its channel or reservoir walls as compared to the capillary forces in the associated device. This difference in capillary force may be brought about by several methods. For example, the walls of the outlet and inlet channels or reservoirs may have differing hydrophobicity or hydrophilicity. Alternatively, the cross-sectional area of the outlet channel or reservoir is made smaller, thus exhibiting greater capillary force.

In some embodiments, flow is facilitated by embedded capacitor valves that pump fluids in a separate channel when pressurized. This is achieved by having a series of valves in the bottom that direct a pressurized gas or liquid causing the membrane to deform and squeeze the fluid in the top channel forward. Additional control is provided by having valves in the top layer that can open sequentially.

In certain embodiments, the selective fluid communication in each component of the enclosed microfluidic cassette device can be controlled by one or more piezoelectric gates in the microfluidic channels comprising nanoelectrode modules connected to the CPU and software controller of the overall system, described in more detail below. In certain embodiments, one or more observation stations for video monitoring and evaluating oocytes, sperm, and embryos are encompassed in one or more component or station in the enclosed microfluidic cassette device.

The invention further provides a system for automated intracytoplasmic sperm injection assisted fertilization comprising the enclosed microfluidic cassette device of the invention and a machine for functionally engaging the microfluidics cassette device comprising a central processing unit (CPU) and software for automated monitoring and control of selective communication for progression of microfluidics, oocyte cumulus removal, oocyte selection and immobilization, motile spermatozoa isolation, motile sperm immobilization, intracytoplasmic sperm injection, and embryo monitoring.

In certain embodiments, the machine of the inventive automated system for intracytoplasmic sperm injection assisted fertilization contains a receptacle, or docking station, for integrating the disposable microfluidics cassette device. The machine can further comprise a plurality of digital video cameras and remote video monitors connected to the CPU and software for visualizing and recording cells at the various corresponding stations within the cassette. In certain embodiments, the CPU and software automatically controls the temperature, pH and pressure of the device and the addition of cellular media to the oocyte reservoir and spermatozoa reservoir, or at any selected point along the pathway.

In some embodiments, the machine of the inventive automated system for intracytoplasmic sperm injection assisted fertilization controls the oocyte immobilizing station by creating negative pressure (a vacuum) through a microchannel in the oocyte immobilizing station of the microfluidic cassette. In some embodiments, the machine of the inventive automated system for intracytoplasmic sperm injection assisted fertilization controls the intracytoplasmic sperm injection by applying an electric field from a pizeo-pipette to penetrate the oocyte and then applying microfluidic pressure inside the pizeo-pipette to position the spermatozoa into the oocyte.

The invention further provides methods for automated intracytoplasmic sperm injection assisted fertilization comprising combining a spermatozoa and an oocyte in a continuous path microfluidics cassette device with the system described herein. Methods for the manufacture of cassette devices, machines and systems for ICSI, as described herein are also provided by the invention.

Various non-limiting embodiments of the devices are depicted in FIGS. 1-17, which are referenced herein. The enclosed microfluidics cassette device of the invention for intracytoplasmic sperm injection assisted fertilization comprises: a) an oocyte reservoir (100) comprising an oocyte chamber (101), an inlet (102) and an outlet (103); b) an oocyte cumulus removal channel (104) in selective fluid communication with the oocyte reservoir outlet; c) an oocyte immobilizing station (120) in selective fluid communication with the oocyte cumulus removal channel; d) a spermatozoa reservoir (200) comprising a spermatozoa chamber (201), an inlet (202) and outlet (203); e) a motile spermatozoa isolating channel (204) in selective fluid communication with the sperm reservoir outlet; f) a motile spermatozoa immobilization station (220) in selective fluid communication with the motile spermatozoa isolating channel and in selective fluid communication with the oocyte immobilization station; and g) an embryo culturing chamber (300) in selective fluid communication with the oocyte immobilization station.

Once oocytes and sperm are placed in their respective chambers (101, 201) of the device, the system can be sealed and activated, and the following steps can be carried out through an automated system whereby individual steps can also be monitored for manual over-ride. Of course, certain modifications of the process would be expected to be within the skill of those in the art, and therefore within the scope of the present invention.

Cumulus-oocyte-complexes (COCs) (106) are cultured and monitored until they reach metaphase II, at which point they must be decoronized and the cumulus cells removed. A denudation or vibration modular chamber (109) can be temporarily created by means of one or more valves (112), as depicted in different embodiments in FIGS. 3, 4 and 5, or a region of the device as depicted in FIG. 1. Hyaluronidase (110) can be added to the denudation chamber in order to decoronize the oocytes. Time of incubation with the hyaluronidase solution can be for example between 2 minutes and 15 minutes; between 5 minutes and 12 minutes, and between 7 minutes and 11 minutes. The hyaluronidase can be recombinant. The concentration of hyaluronidase per oocyte can be between 10 IUs per ml and 40 IUs per ml. The denudation chamber or region can then be vibrated in order to further clean the oocyte, and vacuum (113) can be applied (as shown in FIGS. 1, 3, and 5) to remove debris, which can be deposited into a waste chamber (105) as shown in FIG. 4, or through the cumulus channel outlet (115), as shown in FIGS. 3, 5, 8, 13, and 14.

Figure 8:
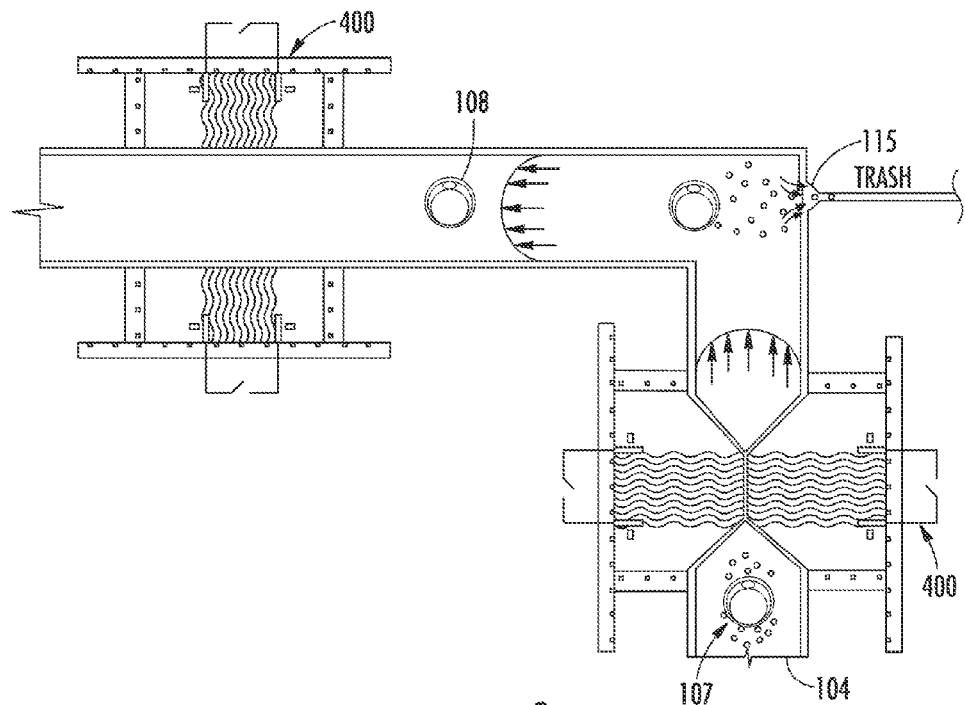
FIG. 8 illustrates secondary cumulus cell removal chamber. In this section, piezoelectric gates are used to create isolated chamber where the completion of removal of cumulus cell is done through suction. Nanoelectrodes modules built-in the PDMS induce a narrowing/closure of the channel. Progression through the channel is sustained by microfluidic flow.
Figure 13:
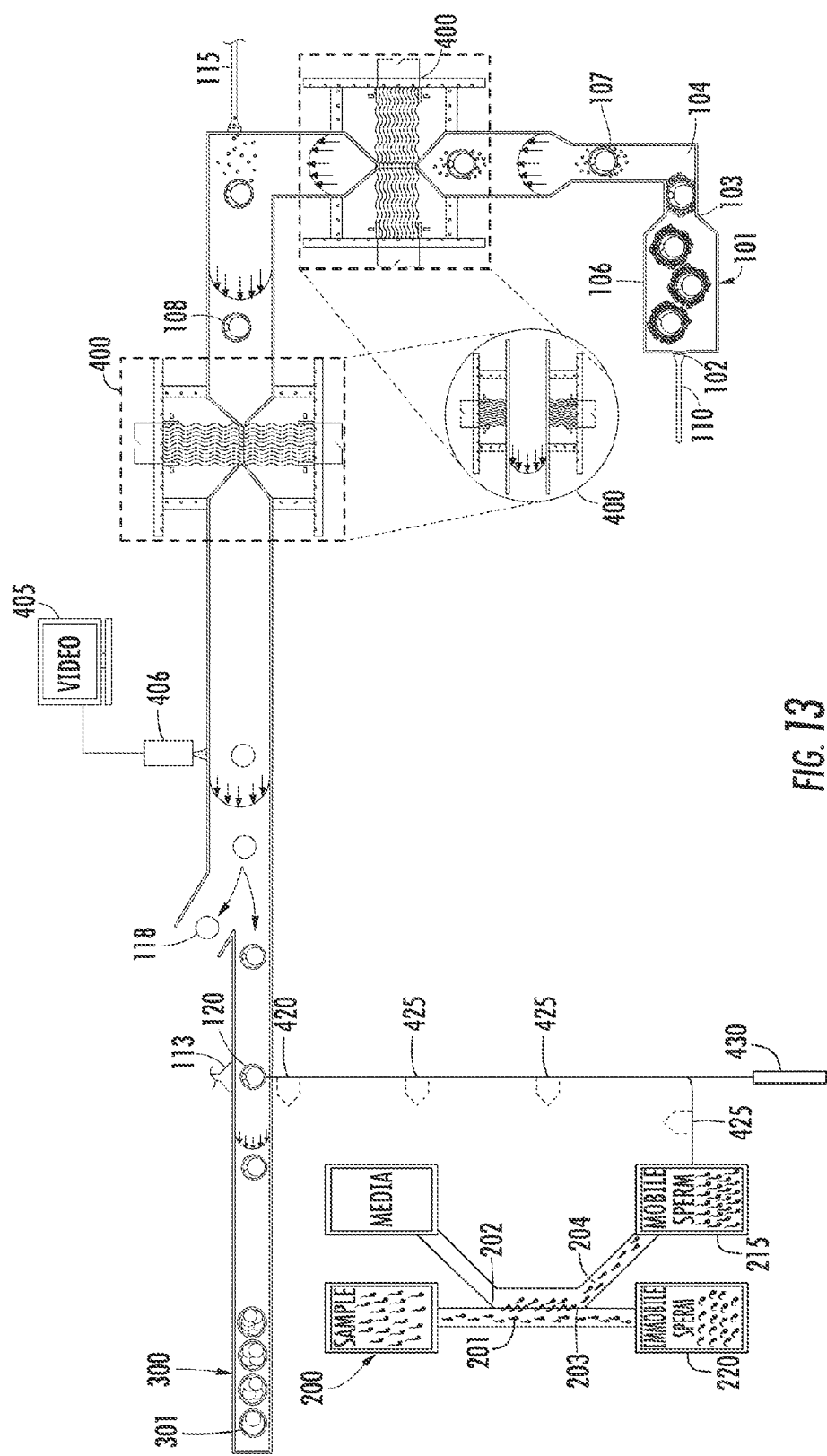
FIG. 13 illustrates the whole microfluidic cassette chip system comprising the lower compartment for oocyte cumulus removal chambers, the center compartment for oocyte maturation assessment, the left compartment for sperm selection, ICSI injection, and an upper compartment for embryo culture.
Figure 14:
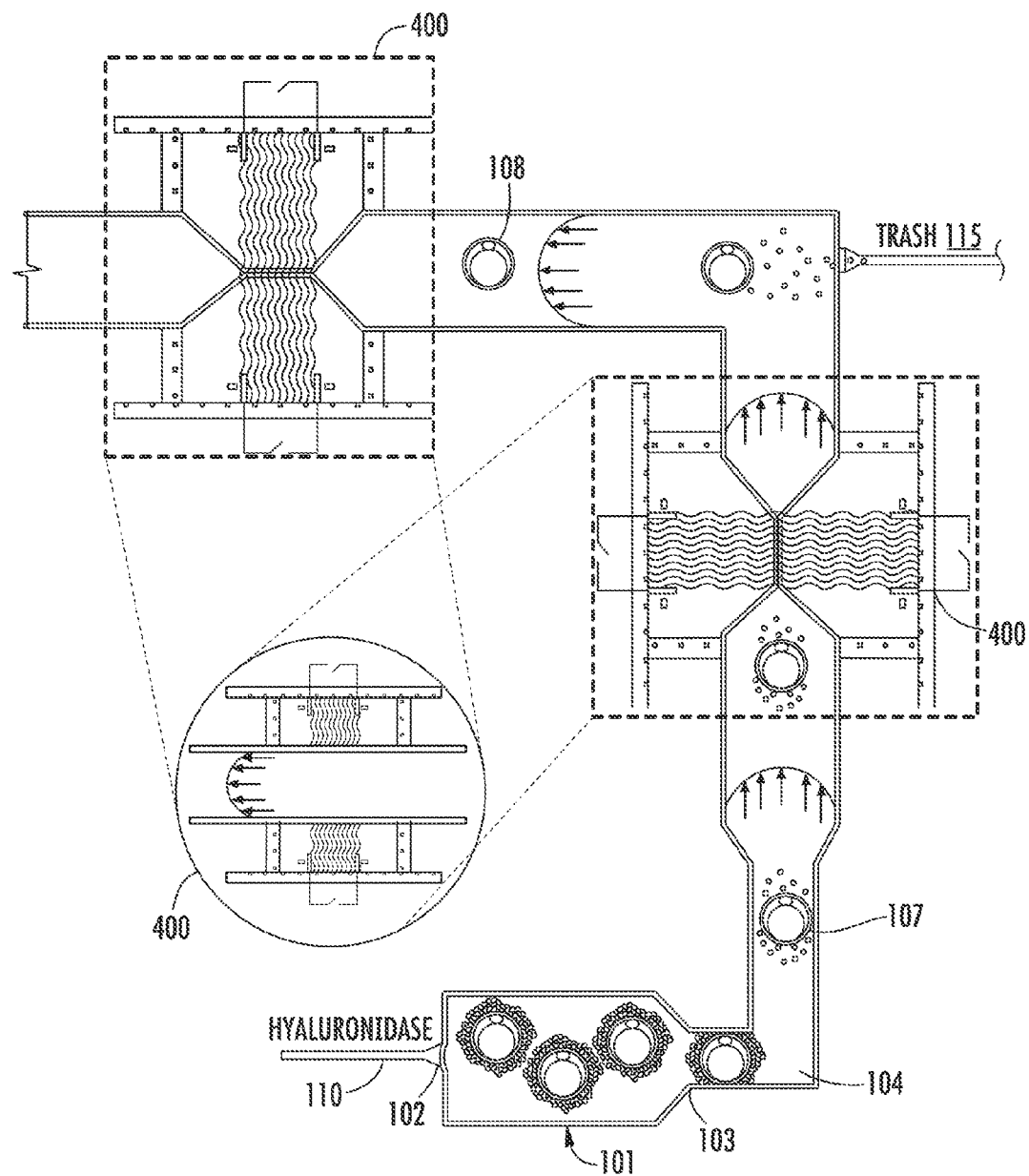
FIG. 14 illustrates the compartment for oocyte cumulus removal chambers and gates.
Figure 15:
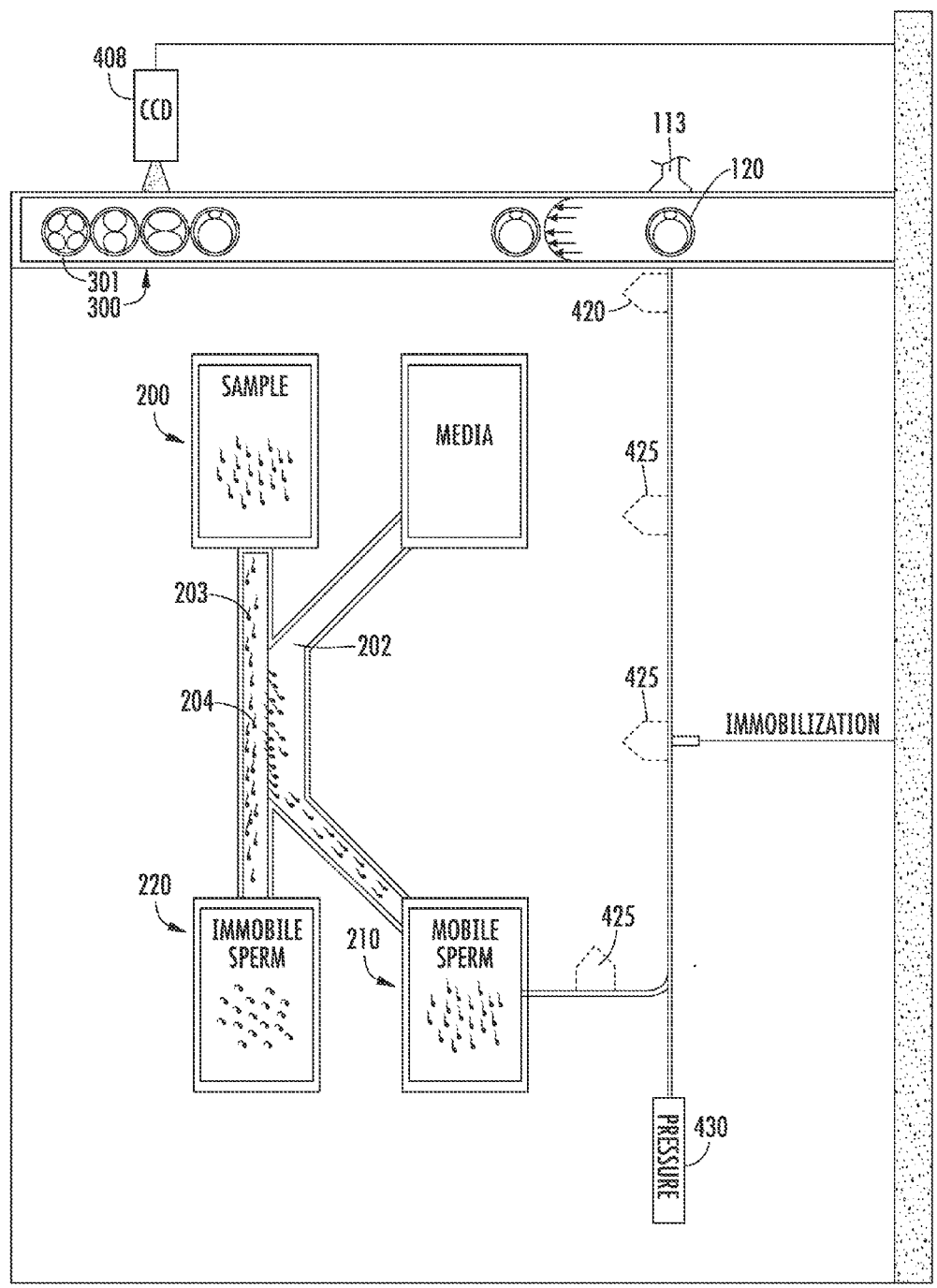
FIG. 15 illustrates the compartment for sperm selection, immobilization, ICSI injection, and embryo culture.

Decoronization can be further aided by passage through a narrow channel (104) controlled by pressure gradient via one or more piezo electric gates (400), as shown in FIGS. 8, 13, and 14. After the hyaluronidase solution is flushed, the denuded oocyte (107) is allowed to rest in fresh media for a period of about 2 hours. Denuded oocytes can also be guided into a modular chamber (109) wherein a flooding of cryo-preservant gradients would allow vitrification of the modular chamber with specimen in it.

Cells can be driven through the chip through microfluidic flow, by means of a peristaltic pump, by pressure gating, or by controlling an electromagnetic field. If the device is made from an elastic compound, including but not limited to PDMS, selected sections of it can be mechanically compressed or released to control valves, facilitate passage, and facilitate peristaltic progression.

Figure 3:
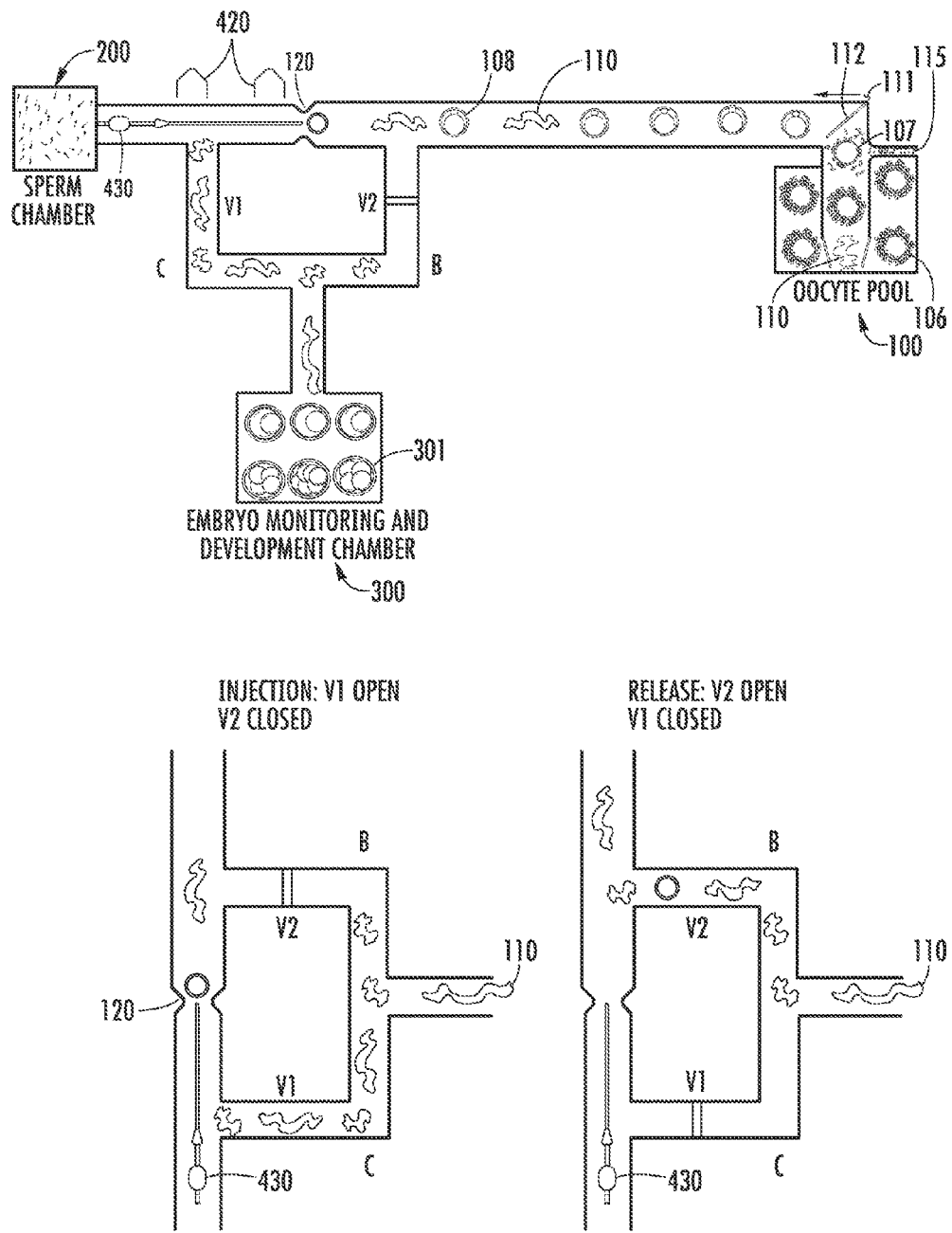
FIG. 3 shows a schematic of an embodiment of the invention in top view, comprising sperm and oocyte chambers, a piezo device, a chamber in which the cumulus-oocyte complex is decoronized and cumulus cells are removed, with outlet to a waste chamber; a configuration and region in which the oocyte is demobilized and the sperm injected, and an embryo monitoring and development chamber. Further depicted is a configuration and valve system for allowing fertilized oocytes to move to the embryo monitoring and development chamber. Further depicted are a pipette for injecting the sperm; a laser sperm immobilization device; and a laser sperm capture and positioning device.
Figure 4:
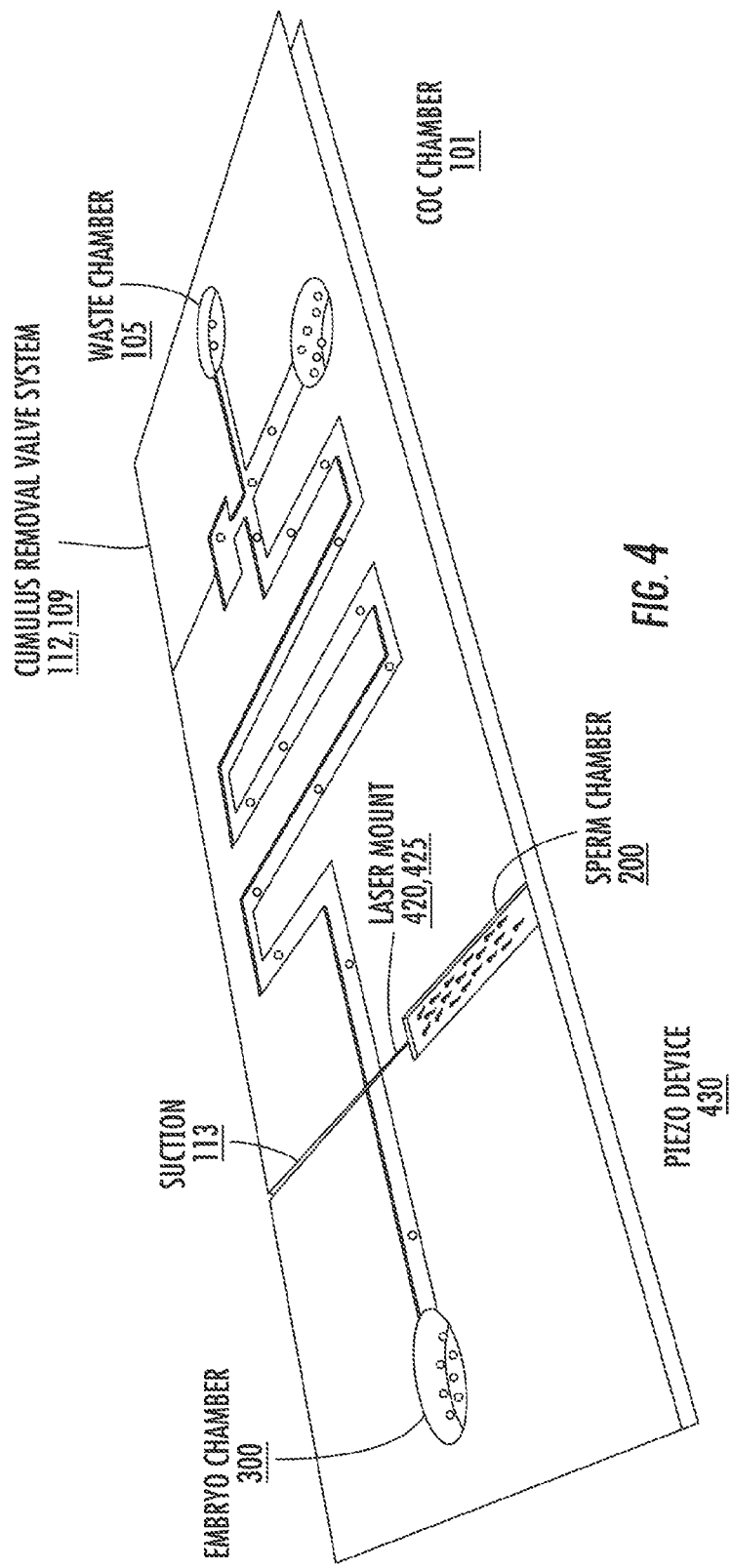
FIG. 4 shows an orthogonal view of an embodiment of the system, comprising sperm and cumulus oocyte complex chambers, a piezo device, a chamber in which the cumulus-oocyte complex is decoronized and cumulus cells are removed, with outlet to a waste chamber; a waste chamber; a configuration and region in which the oocyte is demobilized and the sperm injected; a suction device for immobilizing the oocyte; and an embryo monitoring and development chamber. A laser sperm immobilization device and a laser sperm capture and positioning device are also depicted. Further depicted are a pipette for injecting the sperm; a laser sperm immobilization device; and a laser sperm capture and positioning device.
Figure 5:
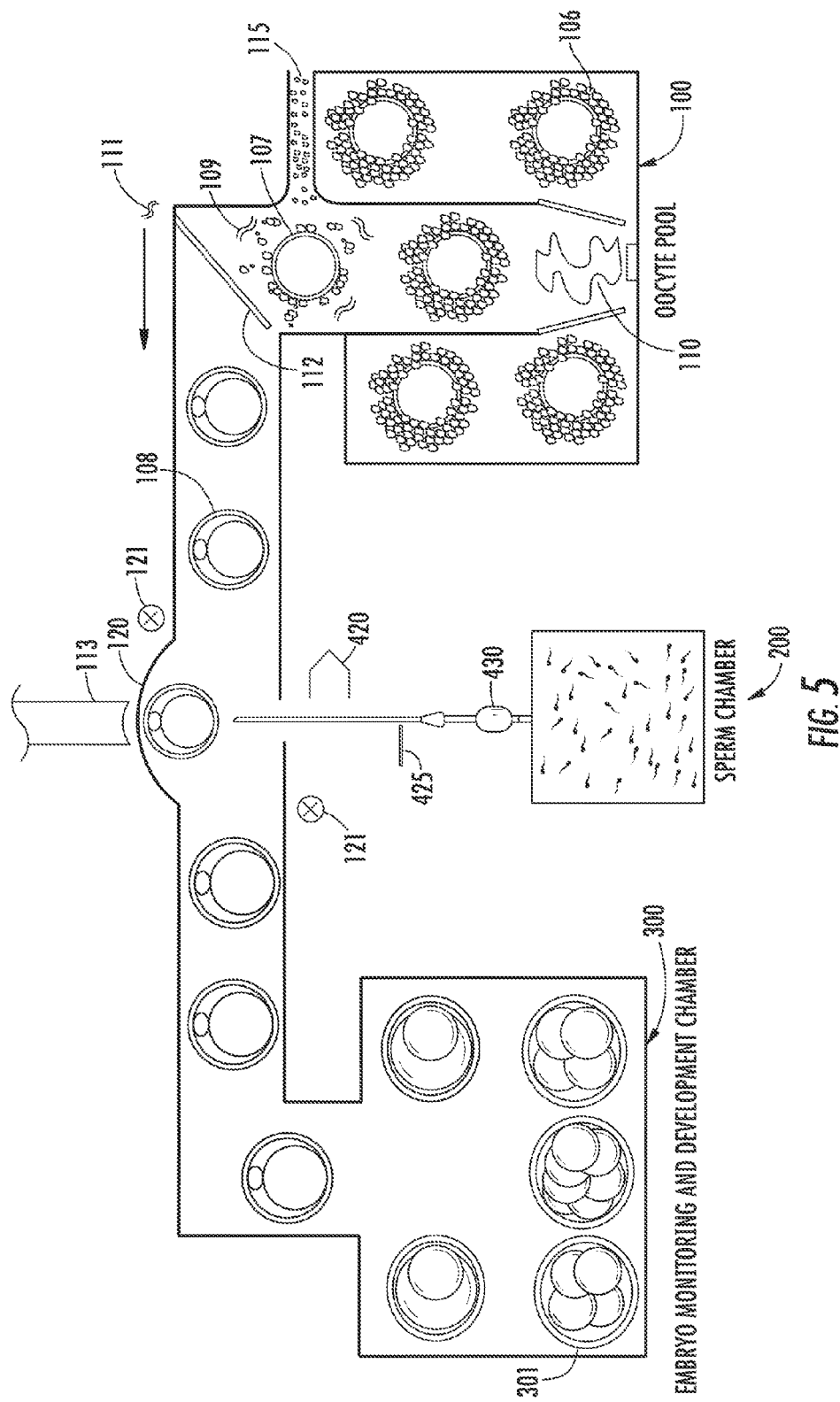
FIG. 5 is a top view of an embodiment of the system, comprising sperm and cumulus oocyte complex chambers, a three valve denudation chamber with a waste channel and channel for adding and eliminating media; a piezo device; a configuration and region in which the oocyte is demobilized and the sperm injected; a suction device for immobilizing the oocyte; and an embryo monitoring and development chamber. A pipette for injecting sperm and a laser sperm immobilization device and a laser sperm capture and positioning device are also depicted. Two electrodes (circles containing an X) are also depicted.
Figure 6:
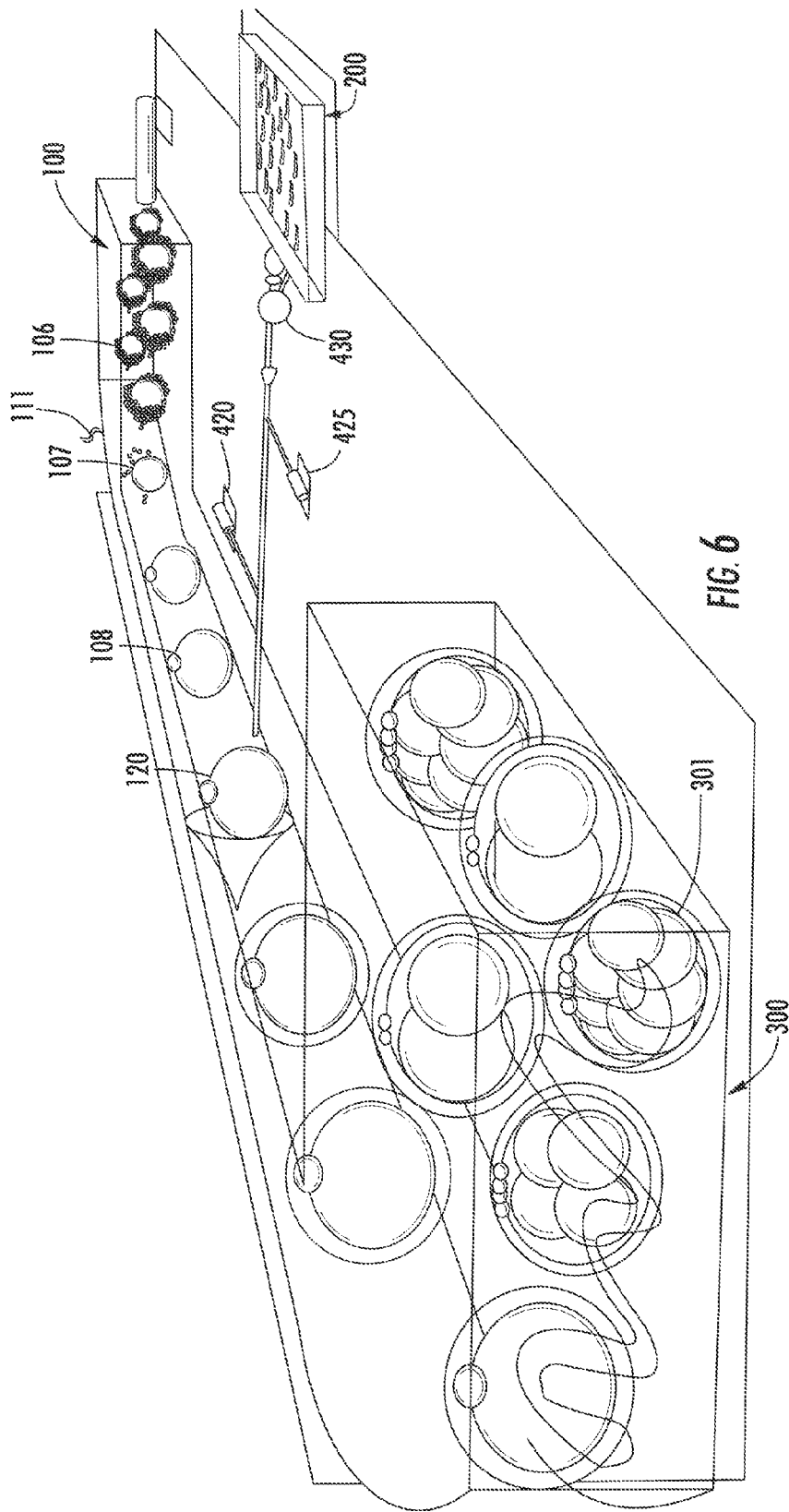
FIG. 6 is an orthogonal view of an embodiment of the system shown in FIG. 5. More noticeable from this perspective is the laser-assisted sperm immobilization and alignment component, which is facilitated via light emission devices along the length of the injection pipette prior to injection.

After denuded metaphase II oocytes reach the oocyte immobilization station for injection, which may be formed by a depression in a chamber wall or by at least one projection from the chamber wall or walls, as shown in FIGS. 1, 2, 3, 5 and 6, they can be aligned via electrical current, such as direct current (DC) alignment (111) along an injection path. The fully denuded metaphase II oocyte (108) can be immobilized by means of a suction device (113) as shown in FIGS. 1, 4, 5 and 11 or by the force of fluid flow as shown in FIG. 3. The polar body of the fully denuded metaphase II oocyte (108) can be aligned for appropriate injection by applying an alternating current across the electrodes (121) as shown in FIG. 5. These electrodes can also be located across the orthogonal diagonal of the oocyte or in any other orientation so as to allow proper orientation of the oocyte.

Figure 10:
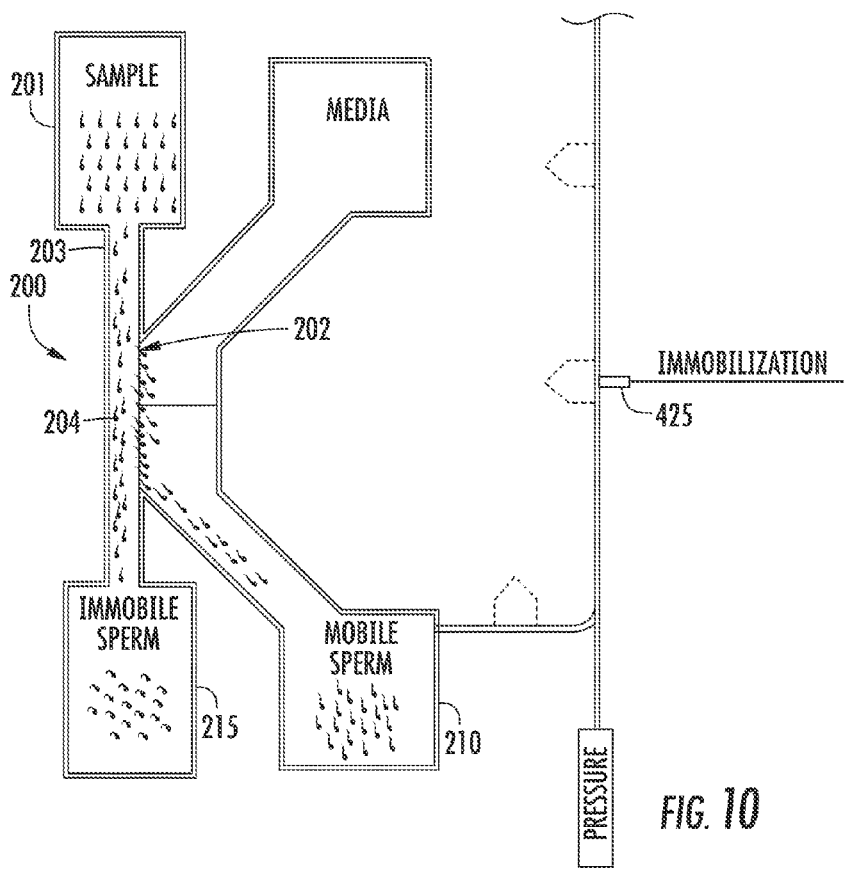
FIG. 10 illustrates sperm selection. The sperm selection is obtained through a gravity-driven pumping system. The sample is loaded in the A chamber, and fresh media is placed in the chamber B. Only the motile sperm is able to cross the interface of the laminar flow stream, exiting into the chamber C. Immotile sperm, debris and some immotile sperm is collected in the chamber D.

With respect to spermatozoa, after deposition into the sperm chamber (200), sperm cells are sorted and selected sperm are pooled into the injection chamber (201) having an inlet (202) and outlet (203). The sperm injection chamber (201) can be a macular chamber that is approximately 5 microns in depth, in which the sperm reside in a single layer. Individual sperm can then be selected by observing the sperm using a camera (407) and computer-aided analysis software which identifies sperm with the best morphology (shape) and motility. Selected sperm can be trapped with lasers and guided into the pipette. Alternatively, a laminar flow can be created in the sperm chamber and only sperm that are able to cross the lamina are then directed into the pipette, such as shown in FIG. 10.

In the pipette, sperm can be captured and aligned using a laser trapping and movement control system (425), such as is known in the art; said system can be aligned along the length of the pipette. Sperm may be immobilized by using a laser to damage the captured sperm's flagellum or membrane.

Figure 11:
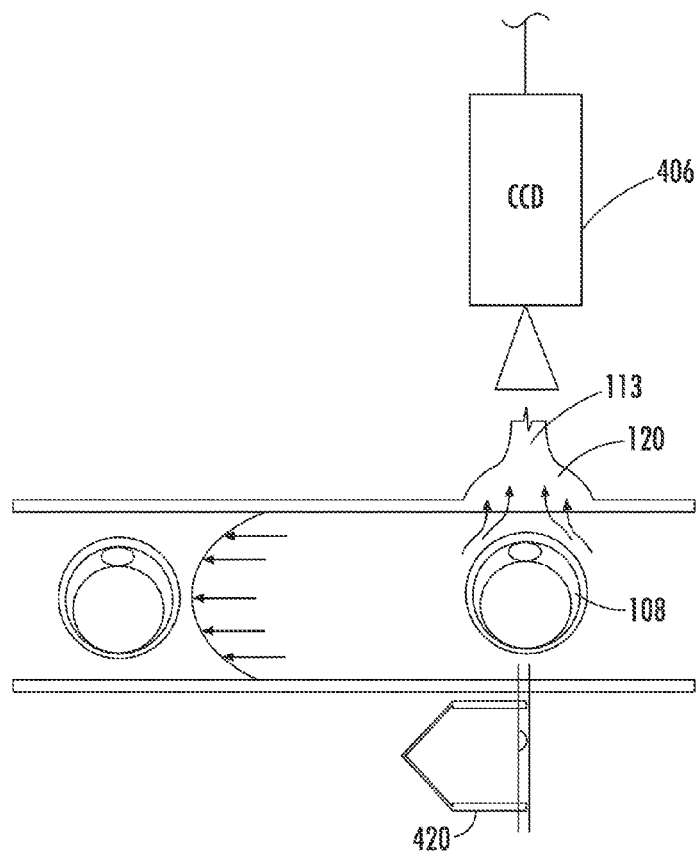
FIG. 11 illustrates ICSI injection. The MII oocyte moved by the microfluidic flow is immobilized by vacuum by a side microchannel. The injection of the single sperm cell is achieved with a piezo-pipette applying first an electric field to penetrate the oocyte and subsequently a flow pressure inside the microtool to position the sperm into the oocyte. A camera system is used to monitor the injection from beginning to end. The oocyte is retrieved by mechanical suction pressure. Progression of the injected oocyte through the microchannel is by microfluidic flow.

The immobilized and aligned oocyte is injected with a blunt pipette shown in FIG. 11, which acts under the control of a piezo device (430) that facilitates penetration of the oocyte, shown in FIGS. 1-6, 11, and 15. The piezo and pipette are in turn mounted on a sliding platform (not shown) that can advance the pipette to the surface of the oocyte and then approximately 75 microns into the human oocyte (30 microns for mouse), under the control of the CPU and software. Successful penetration through the oolemma is confirmed by known patch clamp technologies (not shown).

The region of the chamber wall where the pipette enters the microfluidic chamber can be made of a different material than the rest of the chamber wall in order to allow penetration of the chamber wall and resealing of the chamber wall after the pipette is withdrawn. Alternatively the chamber wall can be comprised of a self-sealing material.

Once all the fertilized oocytes have progressed into the embryo culture chamber (300), the fertilized embryos are cultured for a period of time, which may be approximately 16 to 18 hours. At the end of said period, the embryos are examined to determine if they have developed into zygotes comprising of two distinct polar bodies and two pronuclei. Oocytes that did not fertilize may be automatically selected and removed from the embryo culture system via a waste port (not shown), for example by a laser capture and movement system.

Remaining embryos (301) are cultured through their various stages within the same chamber because refreshing of different types of media can be accomplished through further microfluidic ports. Conditioned medium post-embryo culture can be assessed using metabolomics arrays. If individual embryos are isolated and surgically biopsied in a chamber using a tool similar to the microinjection, the biopsied embryo can be genetically screened. Embryos can also be separated into different chambers for maturation and cryopreservation.

The microfluidic cassette device should be temperature controlled and the medium flowing into it must be monitored for pH and osmolarity variations. The system includes sensors for temperature, pH, osmolarity, and ion transit. The sensors are operable connected via wires, or wirelessly, to the CPU and software control system that monitors each parameter to ensure that they are within human physiological ranges, and if the range is exceeded in either direction, the control system acts accordingly to increase or decrease temperature, pH, osmolarity, and ion transit to keep the system within human physiological parameters.

The system includes reservoirs for at least three fluids. A hyaluronidase solution for cumulus removal; a basic solution such as G1, commercially available from Vitrolife; and an embryo culture solution, such as G2, commercially available from Vitrolife.

Prior to the injection step, the system is filled with G1 solution or its equivalent. Subsequent to completion of all injections, the system is filled with G2 or an equivalent solution. Replacement of the first solution by the second solution may be gradual, for instance taking place over the course of an hour.

The following further provides more detailed descriptions for each compartment of the entire microfluidic cassette of the invention, as shown together in FIG. 13, comprising the lower compartment for oocyte cumulus removal chambers; the center compartment for oocyte maturation assessment; and the left compartment for sperm selection and ICSI, and a compartment for embryo culture shown at the top of the Figure.

Figure 7:
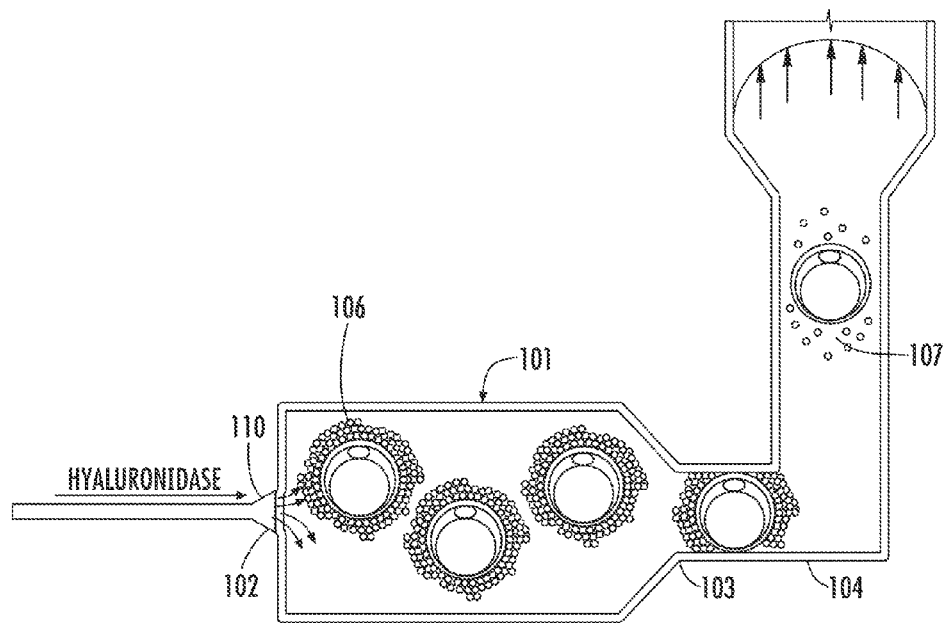
FIG. 7 illustrates cumulus removal. In this chamber, hyaluronidase is flushed through to initiate the removal of the cumulus cells from the egg. The funnel shape of the exit chamber of width ~200 µm will allow individual progression of the egg cells. Progression through the channel is executed by microfluidic flow.

The oocyte cumulus removal chambers and gates are shown in FIGS. 7, 8, and 14. FIGS. 7 and 8 illustrate in more detail the cumulus removal including first and second cumulus removal chambers and gates. Exemplary, non-limiting examples of cumulus removals are provided below. In the chamber shown in FIG. 7 for first/initial cumulus removal, hyaluronidase (110) is flushed through to initiate the removal of the cumulus cells from the egg. In certain embodiments, the funnel shape of the exit chamber (103) of width ~200 μm will allow individual progression of the egg cells. Progression through the cumulus removal channel (104) is executed by microfluidic flow. FIG. 8 illustrates secondary cumulus cell removal chamber, wherein piezoelectric gates (400) are used to create isolated chamber where the completion of removal of cumulus cell is done through suction. Nanoelectrode modules built-in the PDMS induce a narrowing/closure of the channel. Progression through the channel is sustained by microfluidic flow. As discussed, microfluidic flow may be achieved by any suitable methods via passive or active means, including but not limited to, peristaltic pumping in unidirectionally or reverse-exchange mode. The microfluidic flow can be pulsatile or continuous, and is not limited by rate of dynamic flow.

Figure 16:
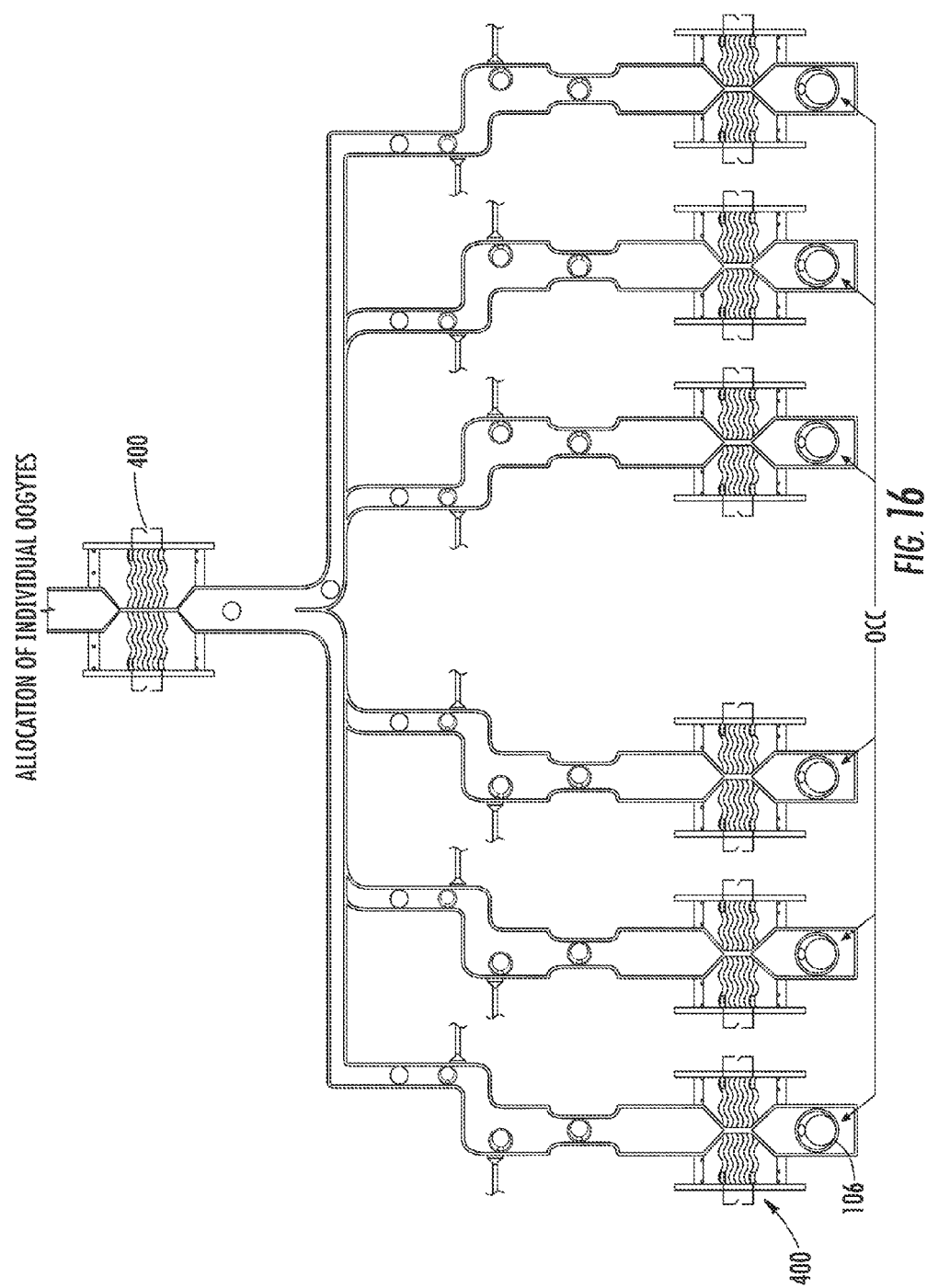
FIG. 16 illustrates allocation of individual oocytes for secondary cumulus removal via multiple microchannels or microchambers with gates.

In certain embodiments, each individual oocyte can be allocated in each microfluidic channel or chamber with gates, as shown in FIG. 16, for initial and/or secondary cumulus removals. In certain embodiment, cumulus removal process can be monitored via video (405) with a computer-assisted program. For exemplary microfluidic devices for cumulus removal from an oocyte, See U.S. Pat. No. 6,695,765 to Beebe, US Publication No. 2007/0264705 to Dodgson; and US Publication No. 2011/0250690 to Craig, each of which is herein incorporated by reference in its entirety.

Figure 9:
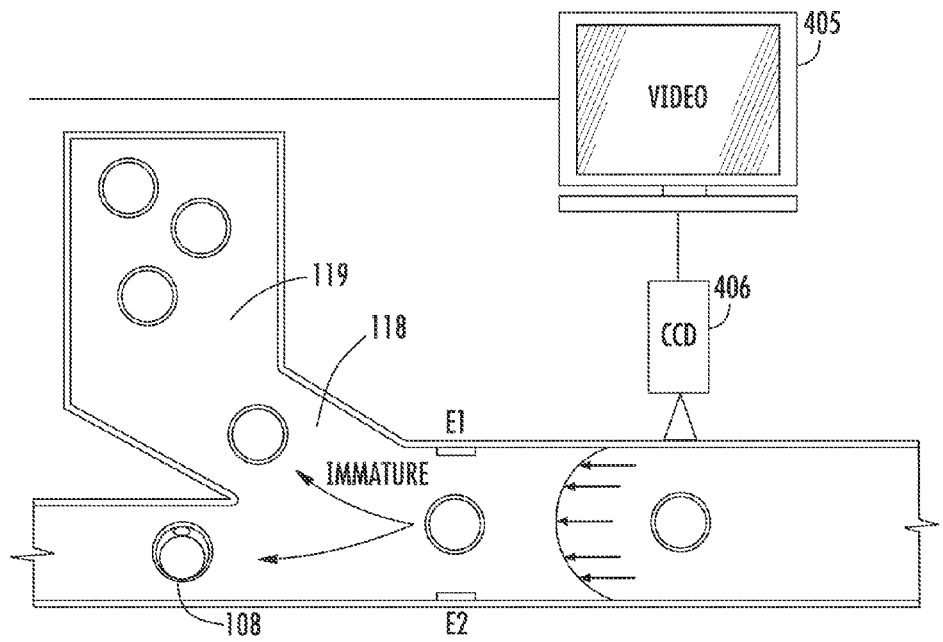
FIG. 9 illustrates egg maturation assessment. In this section oocyte maturity is assessed through a video. The camera connected to a computer processor and software is equipped with a morphology recognition-system that can distinguish whether the cells are carrying a polar body or not. This system, subsequently, send a signal to the software that controls the selection. The holding in place and orientation of the egg is achieved through a pair of electrodes that are contraposed within the channel wall and will allow the delivery of AC current. Allocation to the immature chamber or progression to the injection section is modulated by fluidic motion.

FIG. 9 illustrates egg maturation assessment, wherein the oocyte maturity is assessed through a video (405). The camera (406) connected to a computer software is equipped with a morphology recognition-system that can distinguish whether the cells are carrying a polar body or not. This system, subsequently, sends a signal to the software that controls the selection. The holding in place and orientation of the egg is achieved through electrodes (121) that are contraposed within the channel wall and will allow the delivery of AC current. Allocation to the immature chamber (119) via an oocyte reject outlet (118) or progression to the injection section is modulated by fluidic motion. For more detailed descriptions of microfluidic devices and methods for in vitro mammalian oocyte culture and maturation, See US Publication No. 2013/0034906, herein incorporated by reference in its entirety.

Sperm selection, immobilization, ICSI injection, and embryo culture, is shown in FIGS. 10, 11, 12, and 15. FIG. 10 illustrates sperm selection. In this embodiment, the sperm selection is obtained through a gravity-driven pumping system. The sample is loaded in the spermatozoa injection chamber (201) having an inlet (202) for accepting fresh media, and outlet (203) to allow the motile sperm to cross the interface channel (204) of the laminar flow stream, exiting into the motile sperm chamber (210). Immotile sperm, debris and some immotile sperm is collected in the immotile chamber (215). For more detailed descriptions of sperm isolation, sorting, and selection, See US Publication No. 2006/0270021 to Takayama et al. which is herein incorporated by reference in its entirety.

FIG. 11 illustrates sperm immobilization and ICSI injection. In this embodiment, the MII oocyte (108) moved before by the microfluidic flow is then immobilized in the immobilization station (120) by vacuum (410) by a side microchannel. Sperm can be captured in the immobilization station (220) and aligned using a laser trapping and movement control system, such as laser assisted sperm immobilization (LASI) (425) and laser assisted sperm positioning (LASP) (420) known in the art. The injection of the single sperm cell is achieved with a piezo-pipette applying first an electric field to penetrate the oocyte and subsequently a flow pressure inside the microtool to position the sperm into the oocyte. A camera system (405, 407) is used to monitor the injection from beginning to end. The oocyte is retrieved by mechanical suction pressure. Progression of the injected oocyte through the microchannel is by microfluidic flow. For more detailed descriptions of intracytoplasmic sperm injection (ICSI), See Lu et al. 2011, Robotic ICSI (Intracytoplasmic Sperm Injection), IEEE Transactions of Biomedical Engineering, 58:2102-2108.

Figure 12:
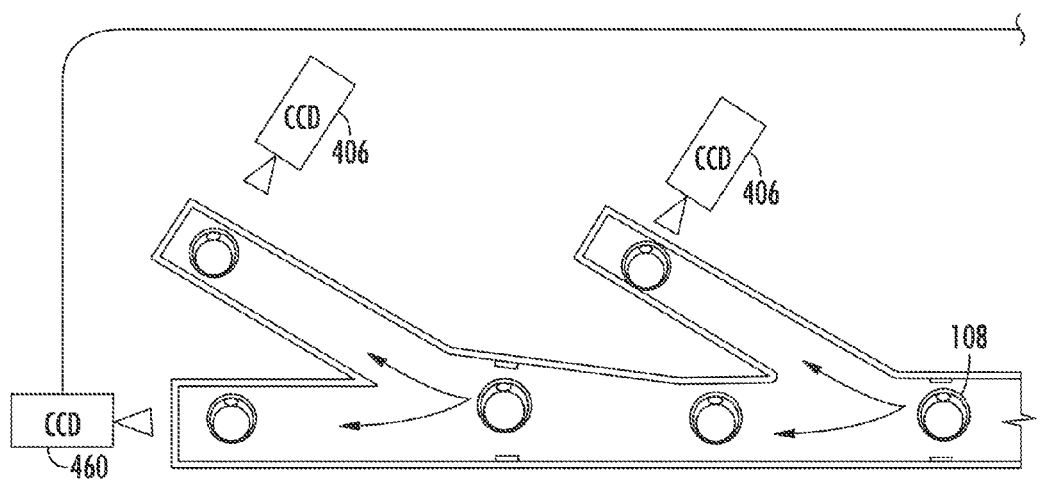
FIG. 12 illustrates embryo culture. After the injection, the oocytes are moved to the end of the microchannel through microfluidic flow and allocated to channel sections. A camera system is used to assay their development until the moment in which it will be selected and used for transfer.
Figure 17:
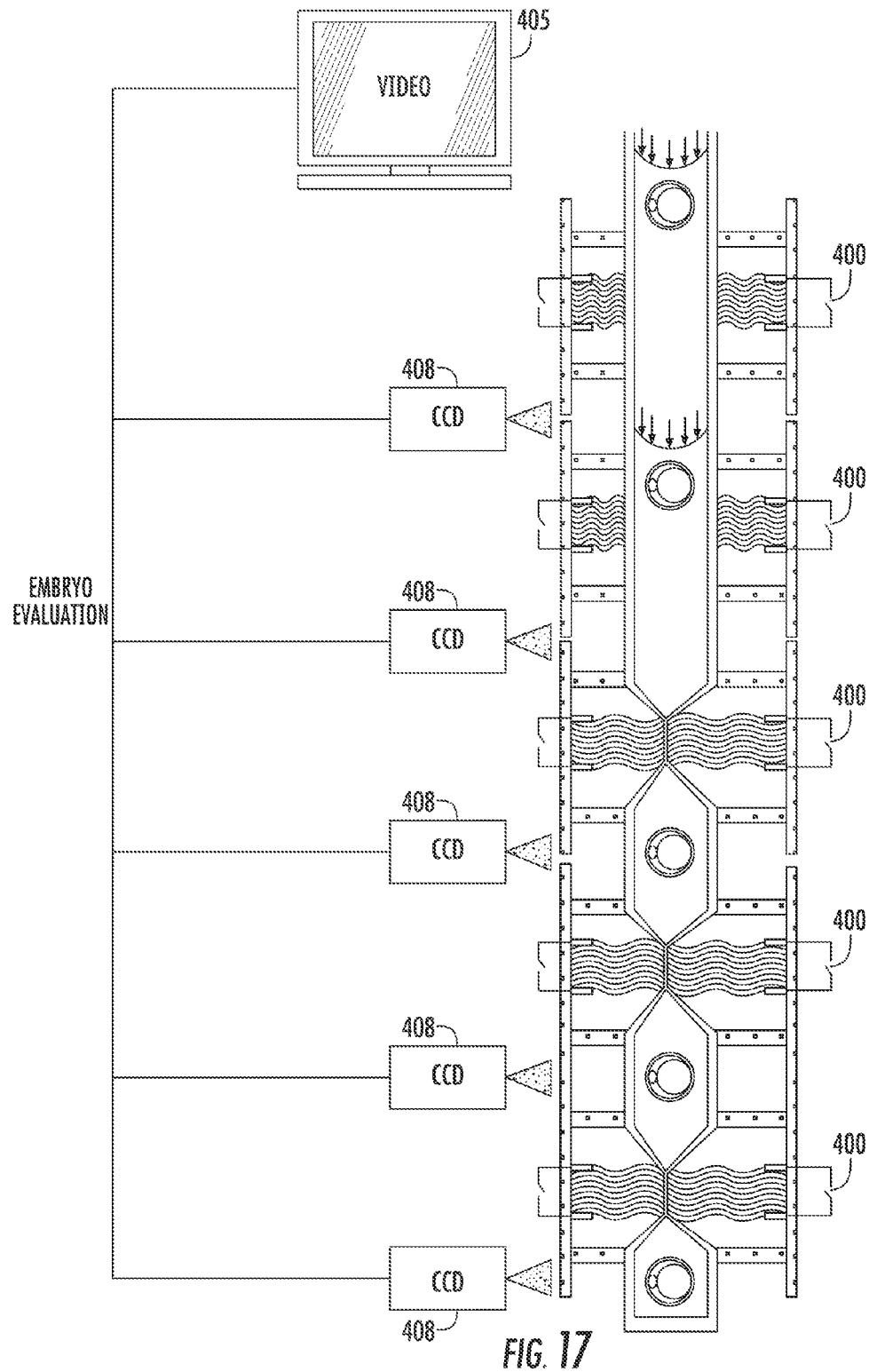
FIG. 17 illustrates monitoring and evaluation of individual embryo via multiple microchannels or chambers.

FIG. 12 illustrates embryo culture. In this embodiment, after the injection the oocytes are moved to the end of the microchannel through microfluidic flow and allocated to channel sections. A camera system (405, 408) is used to assay their development until the moment in which will be picked and used for transfer. Monitoring and evaluation of individual embryo via multiple microchannels or chambers are illustrated in FIG. 17. Culture media and methods for embryo development are well known in the art.

The invention claimed is:

1. An enclosed microfluidics cassette device for intracytoplasmic sperm injection assisted fertilization comprising:
    a) an oocyte reservoir comprising an oocyte chamber, an inlet and an outlet;
    b) an oocyte cumulus removal channel in selective fluid communication with the oocyte reservoir outlet;
    c) an oocyte immobilizing station in selective fluid communication with the oocyte cumulus removal channel;
    d) a spermatozoa reservoir comprising a spermatozoa chamber, an inlet and outlet;
    e) a motile spermatozoa isolating channel in selective fluid communication with the spermatozoa reservoir outlet;
    f) a motile spermatozoa immobilization station in selective fluid communication with the motile spermatozoa isolating channel and in selective fluid communication with the oocyte immobilization station; and
    g) an embryo culturing chamber in selective fluid communication with the oocyte immobilization station.

2. The device of claim 1, wherein a portion of the oocyte cumulus removal channel has a narrower width than the oocyte chamber allowing individual progression of an oocyte.

3. The device of claim 2, wherein a portion of said oocyte cumulus removal channel has a width about 200 mm.

4. The device of claim 1, wherein the oocyte cumulus removal channel has a 90° turn allowing rotation of an oocyte to remove cumulus cells.

5. The device of claim 1, wherein selective fluid communication is controlled by one or more piezoelectric gates comprising nanoelectrode modules.

6. The device of claim 1, wherein the oocyte cumulus removal channel has a waste outlet in selective fluid communication therewith.

7. The device of claim 1, wherein the motile spermatozoa isolating channel has an immotile spermatozoa outlet in selective fluid communication therewith.

8. The device of claim 1, further comprising a plurality of embryo culturing chambers in selective fluid communication with the oocyte immobilization station.

9. The device of claim 1, further comprising one or more embryo observation stations in selective fluid communication with the embryo culturing chamber.

10. The device of claim 1, further comprising one or more sperm observation stations in selective fluid communication with the motile spermatozoa immobilization station.

11. The device of claim 1, further comprising one or more oocyte observation stations in selective fluid communication with the oocyte immobilizing station.

12. The device of claim 1, further comprising a plurality of oocyte reservoirs in selective fluid communication with a plurality of oocyte cumulus removal channels in selective fluid communication with the oocyte immobilizing station.

13. The device of claim 1, wherein the motile spermatozoa immobilization station comprises an intracytoplasmic sperm injection system.

14. The device of claim 1, adapted for insertion into a machine for automated monitoring and control of oocyte cumulus removal, oocyte selection and immobilization, motile spermatozoa isolation, motile sperm immobilization, intracytoplasmic sperm injection, and embryo monitoring.

15. A system for automated intracytoplasmic sperm injection assisted fertilization comprising:
an enclosed microfluidics cassette device for intracytoplasmic sperm injection assisted fertilization comprising:
  a) an oocyte reservoir comprising an oocyte chamber, an inlet and an outlet;
  b) an oocyte cumulus removal channel in selective fluid communication with the oocyte reservoir outlet;
  c) an oocyte immobilizing station in selective fluid communication with the oocyte cumulus removal channel;
  d) a spermatozoa reservoir comprising a spermatozoa chamber, an inlet and outlet;
  e) a motile spermatozoa isolating channel in selective fluid communication with the spermatozoa reservoir outlet;
  f) a motile spermatozoa immobilization station in selective fluid communication with the motile spermatozoa isolating channel and in selective fluid communication with the oocyte immobilization station; and
  g) an embryo culturing chamber in selective fluid communication with the oocyte immobilization station; and
a machine for functionally engaging the microfluidics cassette device comprising a central processing unit (CPU) and software for automated monitoring and control of selective communication for progression of microfluidics, oocyte cumulus removal, oocyte selection and immobilization, motile spermatozoa isolation, motile sperm immobilization, intracytoplasmic sperm injection, and embryo monitoring.

16. The system of claim 15, wherein the machine further comprises a plurality of video cameras and remote video monitors connected to the CPU.

17. The system of claim 15, wherein the CPU automatically controls the temperature of the device and the addition of cellular media to the oocyte reservoir inlet and spermatozoa reservoir inlet.

18. The system of claim 15, wherein the machine controls the oocyte immobilizing station by creating negative pressure through a microchannel in the oocyte immobilizing station.

19. The system of claim 15, wherein the machine controls the intracytoplasmic sperm injection by applying an electric field from a pizeo-pipette to penetrate the oocyte and then applying microfluidic pressure inside the pizeo-pipette to position the spermatozoa into the oocyte.

20. A method for automated intracytoplasmic sperm injection assisted fertilization comprising:
combining a spermatozoa and an oocyte in a system comprising:
  an enclosed microfluidics cassette device for intracytoplasmic sperm injection assisted fertilization comprising:
    a) an oocyte reservoir comprising an oocyte chamber, an inlet and an outlet;
    b) an oocyte cumulus removal channel in selective fluid communication with the oocyte reservoir outlet;
    c) an oocyte immobilizing station in selective fluid communication with the oocyte cumulus removal channel;
    d) a spermatozoa reservoir comprising a spermatozoa chamber, an inlet and outlet;
    e) a motile spermatozoa isolating channel in selective fluid communication with the spermatozoa reservoir outlet;
    f) a motile spermatozoa immobilization station in selective fluid communication with the motile spermatozoa isolating channel and in selective fluid communication with the oocyte immobilization station; and
    g) an embryo culturing chamber in selective fluid communication with the oocyte immobilization station; and
  a machine for functionally engaging the microfluidics cassette device comprising a central processing unit (CPU) and software for automated monitoring and control of selective communication for progression of microfluidics, oocyte cumulus removal, oocyte selection and immobilization, motile spermatozoa isolation, motile sperm immobilization, intracytoplasmic sperm injection, and embryo monitoring.

* * * * *